United States Patent [19]

Warawa

[11] 4,046,892
[45] Sept. 6, 1977

[54] 7-AZA-11,12-DIOXA-6-PHENYL-TRICYCLO[7,2,1,0$^{1.6}$]DODECANE DERIVATIVES AND PROCESS FOR THEIR PREPARATION

[75] Inventor: Edward John Warawa, Libertyville, Ill.

[73] Assignee: Abbott Laboratories, North Chicago, Ill.

[21] Appl. No.: 670,192

[22] Filed: Mar. 24, 1976

[51] Int. Cl.$^2$ .................. C07D 498/08; A61K 31/535
[52] U.S. Cl. ............................... 424/248.57; 544/101
[58] Field of Search .................. 260/244 R; 424/248, 424/248.57

[56] References Cited

U.S. PATENT DOCUMENTS 3,951,968  4/1976  Fauran et al. .................. 260/244 R

*Primary Examiner*—Henry R. Jiles
*Assistant Examiner*—R. W. Ramsuen
*Attorney, Agent, or Firm*—Paul D. Burgauer; Robert L. Niblack

[57] ABSTRACT

A limited class of novel compounds, the 7-aza-11,12-dioxa-6-phenyl-tricyclo[7,2,1,0$^{1.6}$]dodecanes carrying an optional alkyl substituent in the 7-position, has been found highly useful as injection anesthetics.

11 Claims, No Drawings

7-AZA-11,12-DIOXA-6-PHENYL-TRICYCLO[7,2,1,0¹,⁶]DODECANE DERIVATIVES AND PROCESS FOR THEIR PREPARATION

DETAILED DESCRIPTION OF THE INVENTION

The development of general anesthetics for the relief of pain associated with surgical procedures represents one of the oldest and most successful areas in the field of medicinal chemistry. With the diversity of chemical structures now comprising this class of pharmaceuticals, it is ironical that one of the oldest agents nitrous oxide, a gas, is still widely used as the agent of choice in a number of surgical procedures.

General anesthetics are agents which reversibly produce a state of unconsciousness and absense of pain sensation. In general, the depth of anesthesia depends upon the dose of the agent used, but the overall pharmacological effects are a property of the specific agent employed as well as of the dose. In addition to their primary action as depressants of the central nervous system, general anesthetics also alter a variety of noncentral functions controlled by several target organs which provide distinct pharmacological profiles for each of the various compounds in this class.

The criteria for an ideal general anesthetic agent can be made according to the needs of the patient, anesthesiologist and the surgeon. As far as the patient is concerned, the agent should provide a pleasant induction, be rapid in onset, allow an uneventful recovery and, above all, it must be safe. From the anesthesiologist's point of view, it should have a wide clinical margin of safety, enable moment to moment control of the depth of anesthesia, permit high oxygen levels and be non-explosive. In order to perform his tasks, the surgeon prefers that the patient feels no pain, lies still to invasive instruments such as the scalpel, has good skeletal muscle relaxation and minimal reflex activity and that the agent does not induce bleeding. As yet, no general anesthetic meets all the criteria of the ideal agent and thus, the search is still continuing.

The general anesthetics are usually classified according to route of administration. These are the inhalational type, composed of both gaseous and volatile liquid agents and the noninhalational type, usually administered by the intravenous or intramuscular route of administration. The current invention is directed to the non-inhalation type of anesthetics useful for parenteral administration.

It has been found that compounds of the formula

I wherein R is hydrogen or loweralkyl and acid addition salts thereof produce the desired anesthetic effect at low dosages and without pain at the site of injection, without after-effect and with almost instant onset of action.

While the compounds of formula I are depicted as the free base, the preferred compounds for inducing anesthesia are their addition salts with physiologically acceptable salts, i.e., the hydrochloride, sulfate, phosphate, citrate, maleate, succinate and acetate salts of I.

The new compounds are extremely stable to storage, either as free bases or as acid addition salts thereof. Surprisingly, the ketals of structure I may be refluxed in 2N acid for several hours without causing appreciable degradation or ring opening. The above compounds have a very fast onset of effect, the effect lasting for several minutes or one hour or longer, depending on the administered initial dose. Of course, the surgeon may repeat the dose if the surgical procedure lasts longer than expected. The anesthiologist has a wide latitude in this respect as the new compounds have an intravenous $LD_{50}$ of $>50$ mg/kg while the effective intravenous dose is only about 15% thereof.

Since the salts mentioned of I are highly water soluble injectable solutions of a wide range of concentrations can be prepared. A practical and preferred range consists in a concentration of 0.1-10% weight by volume solution which may contain the usual additives often employed in this type of a drug, i.e., salt to produce an isotonic ion concentration, stabilizers, preservatives, buffers and the like, although none of these agents are required for the purpose of comfort to the patient.

In a general embodiment, the compounds of formula I are prepared by treating 2-amino-(or 2-alkylamino)-2-phenylcyclohexanone with epibromohydrin in the presence of a suitable reaction medium and an acceptor for HBr. Refluxing for several hrs. produces the ketal of formula I wherein R is alkyl. Treating this compound with potassium permanganate produces two components, the 7-formyl derivative of I and the 8-oxo-analog of I. The former converts readily to I (R = H) by treatment with 1N methanolic hydrogen chloride which treatment does not affect the 8-oxo-analog. The latter, however, can be hydrogenated with borane to produce I (R = alkyl) again so that substantially no loss occurs.

In order to illustrate the process for making the compounds of the current invention, reference is made to the following examples, which, however, are not intended to limit the scope of the invention in any respect.

EXAMPLE 1

A solution of 8.18 g of 2-methylamino-2-phenylcyclohexanone and 6.03 g of epibromohydrin and 4.45 g of triethylamine in 30 ml of toluene was refluxed for 18 hrs. The mixture was cooled and decanted through the insoluble material. The solid was triturated several times with benzene and the benzene extract was combined with the above toluene solution and concentrated in vacuo. The resulting residue was distilled from a Kuegelrohr at 123°-150° C/0.05 mm to yield 6.72 g of a liquid. The material was dissolved in a minimum amount of methylene chloride and placed on a column containing 80 g of a silica gel. The column was eluted with 150 ml methylene chloride and then with 5% ethyl ether/methylene chloride in fractions of 50 ml. Fractions 4 to 8 yielded 5.53 g of a homogeneous solid (thin layer chromatogram). This material was Kuegelrohr distilled to give 5.16 g (49.7%) of 7-aza-11,12-dioxa-7-methyl-6-phenyltricyclo[7,2,1,0¹,⁶]dodecane; bp: 115°-125° C/0.4 mm.

An etherial solution of 5.0 g of this material was treated with gaseous hydrochloric acid which precipitated a gum that solidified on standing in ethyl ether. This material was triturated with 50 ml of boiling acetone, filtered and dried in a drying pistol over refluxing acetone to yield 4.46 g of the hydrochloride salt of the above compound; mp 228°-229° C.

When in the above Example, the triethylamine was replaced by potassium carbonate, material identical to the above was obtained.

EXAMPLE 2

A solution of 5.32 g of 2-n-butylamine-2-phenylcyclohexanone, 3.3 g of epibromohydrin and 2.5 g of triethylamine in 40 ml of toluene was refluxed for 20 hrs and cooled. Following the procedure of Example 1, 1.07 g of pure 7-aza-7-n-butyl-11,12-dioxa-6-phenyl-tricyclo[7,2,1,0$^{1,6}$]dodecane is obtained; bp 130°-135° C/0.09 mm.

EXAMPLE 3

A solution of 4.8 g of the base made by the process of Example 1 in 500 ml of acetone and 25 ml of glacial acetic acid was stirred with 5.0 g of potassium permanganate for 16 hrs at room temperature and filtered thereafter through hydrated amorphous silica. The filtrate was concentrated in vacuo and the residue was treated in sequence with water, sodium bisulfite, potassium carbonate and then extracted with methylene chloride. The extract was dried over magnesium sulfate, concentrated in vacuo to yield a viscous oil. This material proved to be a mixture of the 7-formyl derivative of I and the 7-methyl-8-oxo derivative of I. The mixture was dissolved in 70 ml of 1N methanolic hydrochloric acid and refluxed for 3½ hrs, at which time thin layer chromatography analysis showed the complete absence of the above formyl derivative. The solvent was then removed in vacuo and the residue was treated with water and extracted with ether. The etherial extract (A) and the water extract (B) were each worked up separately.

Extract A was washed several times with water and subsequently with saturated saline before drying it over magnesium sulfate. The solvent was removed under reduced pressure, yielding 3.45 g of 7-aza-11,12-dioxa-7-methyl-8-oxo-6-phenyltricyclo[7,2,1,0$^{1,6}$]dodecane. A 3-necked flask, equipped with a condenser, addition funnel and magnetic stirrer, was flushed out with nitrogen and 20 ml of dimethoxyethane (DME) and 2.5 ml of borane dimethylsulfide was added. The flask was cooled in ice, and the above dodecanone in 20 ml of DME was placed in the addition funnel and dropped through there into the stirred solution. When the addition was completed, the solution was refluxed for 1 hour, cooled and cautiously treated by drop-wise adding 15 ml of 6N hydrochloric acid. The DME was then removed in vacuo; the residue was treated with aqueous potassium hydroxide solution and extracted with ether, which extract was dried over magnesium sulfate. After removal of the solvent, 3.27 g of I (R = CH$_3$) was recovered.

Extract B was treated with potassium carbonate and extracted with methylene chloride. After drying this extract, the solvent was removed in vacuo to yield 1.33 g of an oil identified as I (R = H), b.p. 128°-133° C/0.05 mm; m.p. (HCl salt): 260°-261° C.

EXAMPLE 4

By repeating the process of Example 1, but using an equimolar amount of 2-amino-2-phenylcyclohexanone as the starting material, the same compound as described in Example 3 (extract B) was obtained, although in a yield considerably lower than that of Example 1.

The above compounds were tested for their anesthetic activity in mice by intravenously administering them as an aqueous solution containing 5% by weight of the hydrochloride of I. In this fashion, the effective dose was established as ED$_{50}$. Compound I (R = H) showed an ED$_{50}$ of 8.5 mg/kg; the hydrochloride of I (R = CH$_3$) showed an ED$_{50}$ of 26 mg/kg. Both compounds almost instantaneously produced the anesthesia level of stage 3, accompanied by muscle relaxation and resembling the effect produced by thiopental. Both compounds are effective in monkeys at 10.9 mg/kg.

In the above examples, only the preparation of the compounds of formula I are their hydrochloride have been described. It will be obvious to those skilled in the art that the corresponding sulfate, phosphate, citrate, acetate and similar physiologically acceptable acid addition salts can be prepared in essentially similar fashion, varying only in some procedural manipulations well within the skill of the artisan.

For the purpose of this specification, the term "loweralkyl" is intended to signify 1 to 4 carbons; for reasons of simplicity in manufacture and therapeutic index, the compounds of formula I, wherein R is hydrogen or methyl, are the preferred species.

In the above examples, the procedures described for making the compounds of this invention, were detailed only in respect to some of the parameters. However, other solvents, temperatures, acid acceptors and reactant ratios may be used. For instance, any inert acid acceptor may be employed. A preferred class thereof are the tertiary organic amines, such as triethylamine, trimethylamine, dimethylcyclohexylamine, pyridine and the like. Another class is represented by the alkali or earth alkali carbonates or bi-carbonates, such as calcium bi-carbonate, potassium carbonate and the like.

In place of the toluene used above, other inert reaction media may be employed, particularly suitable are benzene, xylene, ethers boiling above 80° C including tetrahydrofurane, amides such as dimethylformamide, dimethylacetamide, or the halogenated or nitrated aromatic solvents, including nitrobenzene, dichlorobenzene, etc.

In general, the ratio between the cyclohexanone derivative and the epibromohydrin can be varied to a considerable extent. A preferred range for this reaction comprises the use of 2 to 10% excess of the epibromohydrin on a molecular basis, although an equimolar ratio may be employed. The limit of 10% excess should not be exceeded because secondary reactions may take place between the epibromohydrin and the final product of structure I.

When operating with the above ratio of reactants, both rings of the new compounds form simultaneously, although the reaction requires moderate temperatures for a considerable period of time. The minimum temperature for economical results is about 80° C, and preferably a temperature of 150° C is not exceeded because secondary reactions may take place. Within the temperature range of 80° C to 150° C, the lower temperatures require longer reaction periods, preferably 10 to 30 hrs; within the upper range of the above temperature span, 5 to 15 hrs produce adequate yields of the desired new compounds. Isolation of the tricyclic compound can be done in simple fashion, which is considered completely within the average skill of the artisan. The simplest method consists in evaporating the reaction mixture to dryness and extraction of the active compound by the use of a suitable solvent. Other methods consist in precipitating the active material by the addition of an inert liquid, miscible with the reaction medium in which the compound of formula I is essentially insoluble.

What is claimed is:

1. The compound of the formula

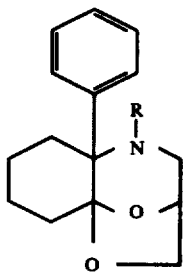

wherein R is hydrogen or loweralkyl or a physiologically acceptable acid addition salt thereof.

2. The compound of claim 1 wherein R is hydrogen.

3. The compound of claim 1 wherein R is methyl.

4. An injectable anesthetic composition containing between 0.1 and 10% by weight of the compound of claim 1 in a liquid, physiologically acceptable diluent.

5. The composition of claim 4 wherein R is hydrogen.

6. The composition of claim 4 wherein R is methyl.

7. The process of preparing 7-aza-11,12-dioxa-6-phenyl-7-alkyl-tricyclo[7,2,1,0$^{1.6}$]dodecane comprising heating a 2-alkylamino-2-phenylcyclohexanone with a 2-10% molecular excess of epibromohydrin in the presence of an inert acceptor for HBr and an inert reaction medium, for 5 to 30 hours to a temperature between 80° C and 150° C.

8. The process of claim 7 wherein said reaction medium is toluene.

9. The process of claim 7 wherein said acceptor is an alkali carbonate or bicarbonate.

10. The process of claim 7 wherein said acceptor is a tertiary amine.

11. The process of claim 10 wherein said acceptor is a triethylamine.